(12) United States Patent
Harris (10) Patent No.: US 11,452,530 B2
(45) Date of Patent: Sep. 27, 2022

(54) CUTTING BLOCK APPARATUS AND METHOD OF TOTAL KNEE ARTHROPLASTY

(71) Applicant: Adam I. Harris, San Antonio, TX (US)

(72) Inventor: Adam I. Harris, San Antonio, TX (US)

(*) Notice: Subject to any disclaimer, the term of this patent is extended or adjusted under 35 U.S.C. 154(b) by 358 days.

(21) Appl. No.: 16/552,027

(22) Filed: Aug. 27, 2019

(65) Prior Publication Data
US 2019/0380719 A1 Dec. 19, 2019

Related U.S. Application Data

(63) Continuation of application No. 15/147,089, filed on May 5, 2016, now Pat. No. 10,413,304.

(51) Int. Cl.
*A61B 17/15* (2006.01)

(52) U.S. Cl.
CPC .................. *A61B 17/155* (2013.01)

(58) Field of Classification Search
CPC ..... A61B 17/15; A61B 17/151; A61B 17/152; A61B 17/154; A61B 17/155; A61B 17/157; A61B 17/158
See application file for complete search history.

(56) References Cited

U.S. PATENT DOCUMENTS

| | | | |
|---|---|---|---|
| 5,662,656 A * | 9/1997 | White | A61B 17/155 606/86 R |
| 5,683,397 A | 11/1997 | Vendrely et al. | |
| 6,013,081 A | 1/2000 | Burkinshaw et al. | |
| 7,641,661 B2 | 1/2010 | Steffensmeier | |
| 8,728,086 B2 | 5/2014 | Smith | |
| 9,693,881 B2 | 7/2017 | Lorio | |
| 11,389,253 B2 * | 7/2022 | Barmes | A61B 5/4887 |
| 2003/0187452 A1 | 10/2003 | Smith et al. | |
| 2014/0148809 A1 | 5/2014 | Schmalzried et al. | |
| 2015/0305752 A1 * | 10/2015 | Eash | A61B 17/151 606/82 |

(Continued)

FOREIGN PATENT DOCUMENTS

FR 2752519 A1 2/1998

OTHER PUBLICATIONS

International Search Report and the Written Opinion dated Aug. 29, 2017 in corresponding international application No. PCT/US2017/031202 (15 pgs.).

*Primary Examiner* — Matthew J Lawson
(74) *Attorney, Agent, or Firm* — Maier & Maier, PLLC (57) ABSTRACT

According to an exemplary embodiment, a cutting block for cutting the femur during knee arthroplasty surgery may be provided. The cutting block may include a cutting guide having a number of slots for guiding a cutter to cut the femur and further comprising a slide extending from the frame of the cutting guide. The cutting block may further include a body that may have a groove with flanges, wherein the space defined by the groove and the flanges may receive the slide extending from the frame of the cutting guide. Further, a feeler gauge may include a support block receiving a pointer arm, wherein the pointer arm may include a pointer that may be configured to make contact with patient bone tissue. A foot including a pair of spaced apart flanges configured to engage the posterior condyles of the patient's femur may also be included in the cutting block.

17 Claims, 8 Drawing Sheets

(56) References Cited

U.S. PATENT DOCUMENTS

| | | |
|---|---|---|
| 2016/0089167 A1 | 3/2016 | Lin et al. |
| 2022/0192774 A1* | 6/2022 | Goble .................... A61B 90/06 |
| 2022/0202458 A1* | 6/2022 | Nachtrab ........... A61B 17/8095 |

* cited by examiner

CUTTING BLOCK APPARATUS AND METHOD OF TOTAL KNEE ARTHROPLASTY

BACKGROUND

Proper placement of components during total knee arthroplasty is critical to obtaining excellent results and avoiding complications. The process of preparation of the bone to accept an implant involves removing the appropriate amount of bone in the proper shape, position, and size for the appropriate implant. Natural knees "come" in an infinite number of different shapes and sizes, while artificial implants, like shoes, may be made only in discrete sizes. A surgeon should select the best fit and place that implant properly and safely.

SUMMARY

According to an exemplary embodiment, a measuring and cutting block and a system for cutting the femur during knee arthroplasty surgery may be provided. The measuring and cutting block may include a cutting guide having a number of slots for guiding a saw blade to cut the femur. The cutting guide may have an anterior face and a posterior face and may include a femoral cut slot extending from the anterior face to the posterior face to guide a saw blade to cut the femur and may further include a slide extending from the frame of the cutting guide. The measuring and cutting block may further include a body that may have a groove with flanges, wherein the space defined by the groove and the flanges may receive the slide extending from the frame of the cutting guide, a locking screw may be threadably engaged in a threaded opening of the body wherein, the locking screw may bear against the cutting guide and may lock the cutting guide against the body. The measuring and cutting block may be calibrated according to the style of implant selected. Further, a feeler gauge may include a support block receiving a pointer arm, wherein the pointer arm may include a pointer that may be configured to make contact with patient bone. A foot piece including a pair of spaced apart projections that may be configured to engage the posterior condyles of the patient's femur may also be included in the cutting block. The feet may set a standard angle, a range of angles, or may be made custom per patient and may be available in a number of sizes for proper fit under the posterior condyles.

According to a second exemplary embodiment, a method of performing a knee arthroplasty surgery on a knee portion of a leg of a patient through an incision may be provided. The method may include assembling the element of a cutting block comprising assembling the elements before placing the feet under posterior condyles and pinning the main block to the distal femur. The feeler gauge may be extended to an approximation of the depth of the anterior cut along the lateral ridge before tightening the screw. Once the screw is secure, the feeler gauge may be removed. The next step may be making the first anterior cut and lowering the cutting guide in small increments to remove more bone anteriorly.

BRIEF DESCRIPTION OF THE DRAWINGS

Advantages of embodiments of the present invention will be apparent from the following detailed description of the exemplary embodiments. The following detailed description should be considered in conjunction with the accompanying figures in which.

DETAILED DESCRIPTION

Aspects of the present invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage, or mode of operation.

Figure 1A:
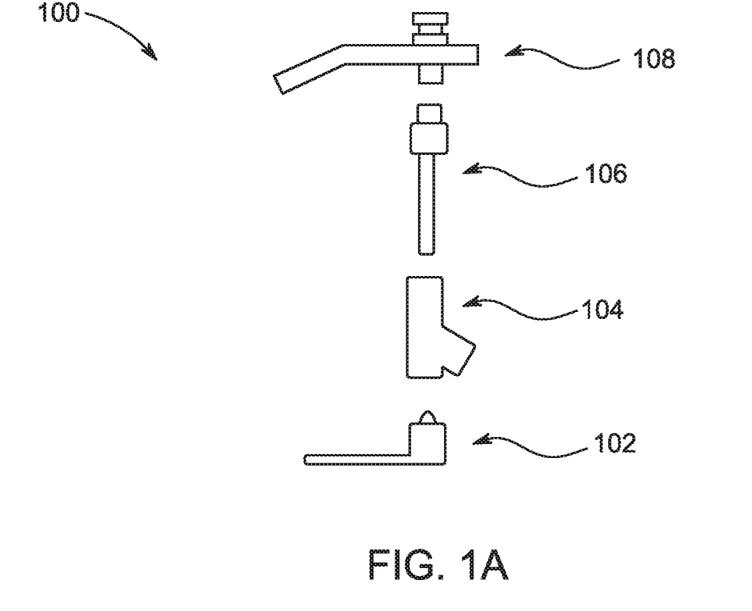
FIG. 1A is a diagram showing a partial side view of an exemplary embodiment of the cutting block for total knee arthroplasty.
Figure 1B:
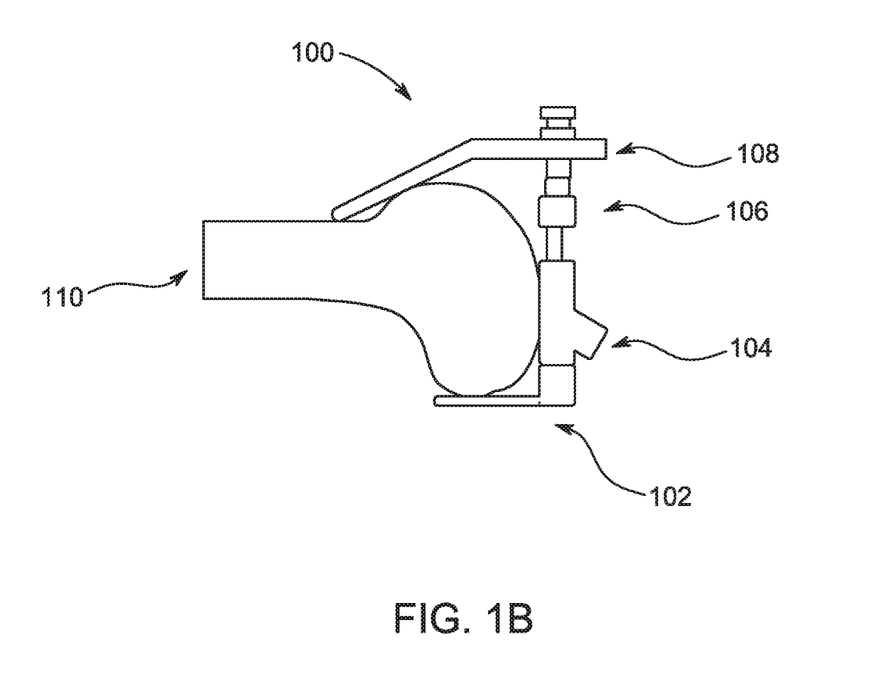
FIG. 1B is a diagram showing a partial side view of an exemplary embodiment of a cutting block for total knee arthroplasty.

According to an exemplary embodiment illustrated in FIGS. 1A and 1B, a measuring and cutting block 100 for knee arthroplasty may be shown and described. The measuring and cutting block 100 may include both anterior and posterior referencing for optimal placement of femoral components and may be designed to make use of a standard distal cut of the femur 110. The system 100 may further include a set of instruments that may measure the rotation of the femoral component using the posterior condyles while the sizing of the component is made anteriorly which may thus optimize the choice of size and the position of the implant. The measuring and cutting block 100 may include, but is not limited to, elements made of metal, such as surgical steel, titanium, or any other desired material, as may be understood by a person of ordinary skill in the art. The measuring and cutting block 100 may include a foot 102, a body 104, a cutting guide 106, and a feeler gauge 108. It may be appreciated that any other elements such as, but not limited to, handles, grips, knobs, bars, pegs, screws, and frames may be incorporated into the cutting block, as may be understood by a person of ordinary skill in the art. Such elements may be used in any of a variety of manners, such as facilitating adjustment of the cutting block, positioning the cutting block, or providing additional gripping or manipulation capabilities.

Figure 2:
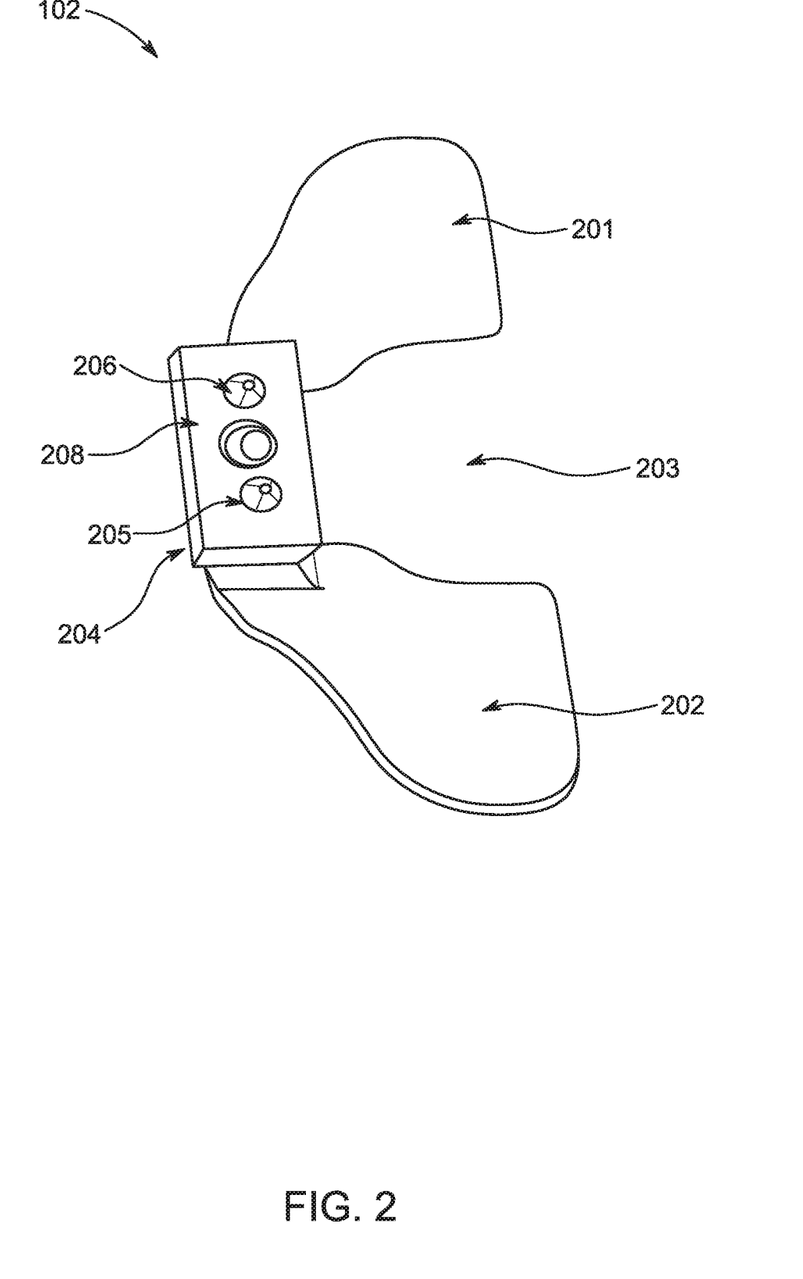
FIG. 2 is a diagram showing an exemplary embodiment of a foot element of the cutting block for total knee arthroplasty.
Figure 8:
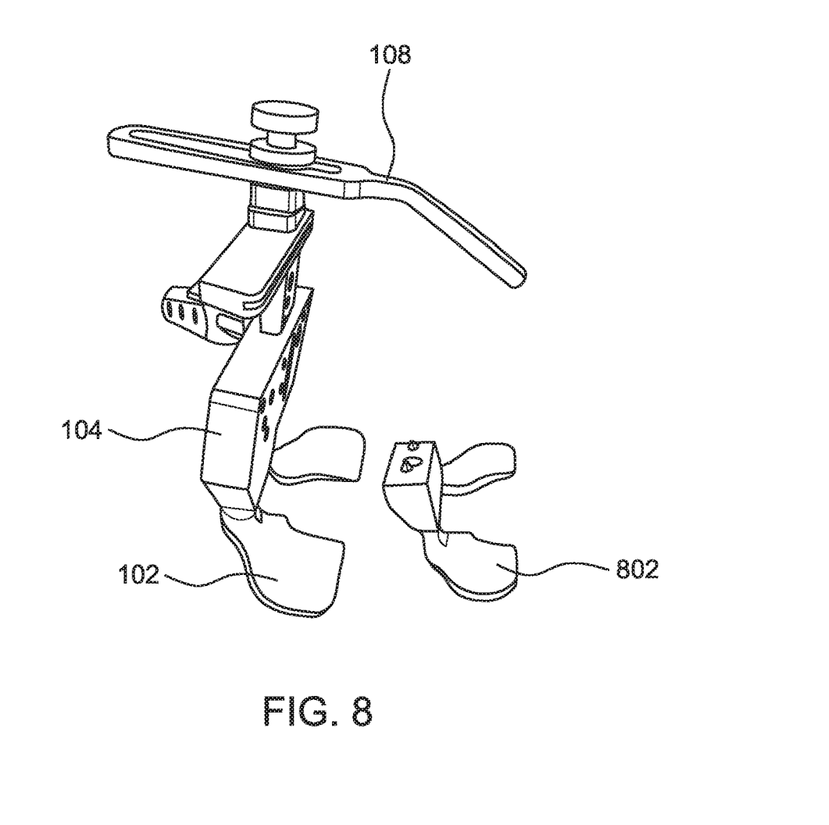
FIG. 8 is a diagram showing an exemplary embodiment of a cutting block for total knee arthroplasty.

In an exemplary embodiment illustrated in FIG. 2, the foot 102 may be used for posterior referencing. Foot 102 may have a curved or contoured surface to protect the tibial surface and allow for the anterior cut to be made with the knee flexed only a few degrees thereby taking tension off the quadriceps mechanism and making exposure easier. As a result of this exemplary configuration, less force may be required on the retractors, which may make recovery easier for the patient. Additionally, foot 102 can be placed with more accuracy and adjusted to be in a most desired position through the use of curved foot 102. The foot 102 may further include a pair of spaced apart projections 201, 202 that may engage the posterior condyles of the patient's femur during referencing. There may be a space 203 between the projections 201, 202. A pair of spaced apart pegs 205, 206 may fit the corresponding openings 408, 409 in the body 104. A base member 204 may extend between the projections 201, 202 and the pegs 205, 206. The base member 204 may provide a flat surface 208 that may register snugly against a flat surface 412 of the body 104. The base 204 may include a threaded opening there through that may receive a fastener (a screw, for example) locking the foot 102 against the body 104. As shown in exemplary FIG. 2, spaced apart projections 201, 202 may be offset by about 2 mm to generate an angle of about 3 degrees. However, in other exemplary embodiments, it may be appreciated that spaced apart projections 201, 202 may be substantially parallel and offset, may be substantially coplanar and set at a predetermined or desired angle, or may be orientated in any other desired or custom fashion, depending on a specific application. Further, as shown in exemplary FIG. 8, spaced apart projections of foot 102 may be formed in any size, for example smaller size spaced apart projections 802.

Figure 3:
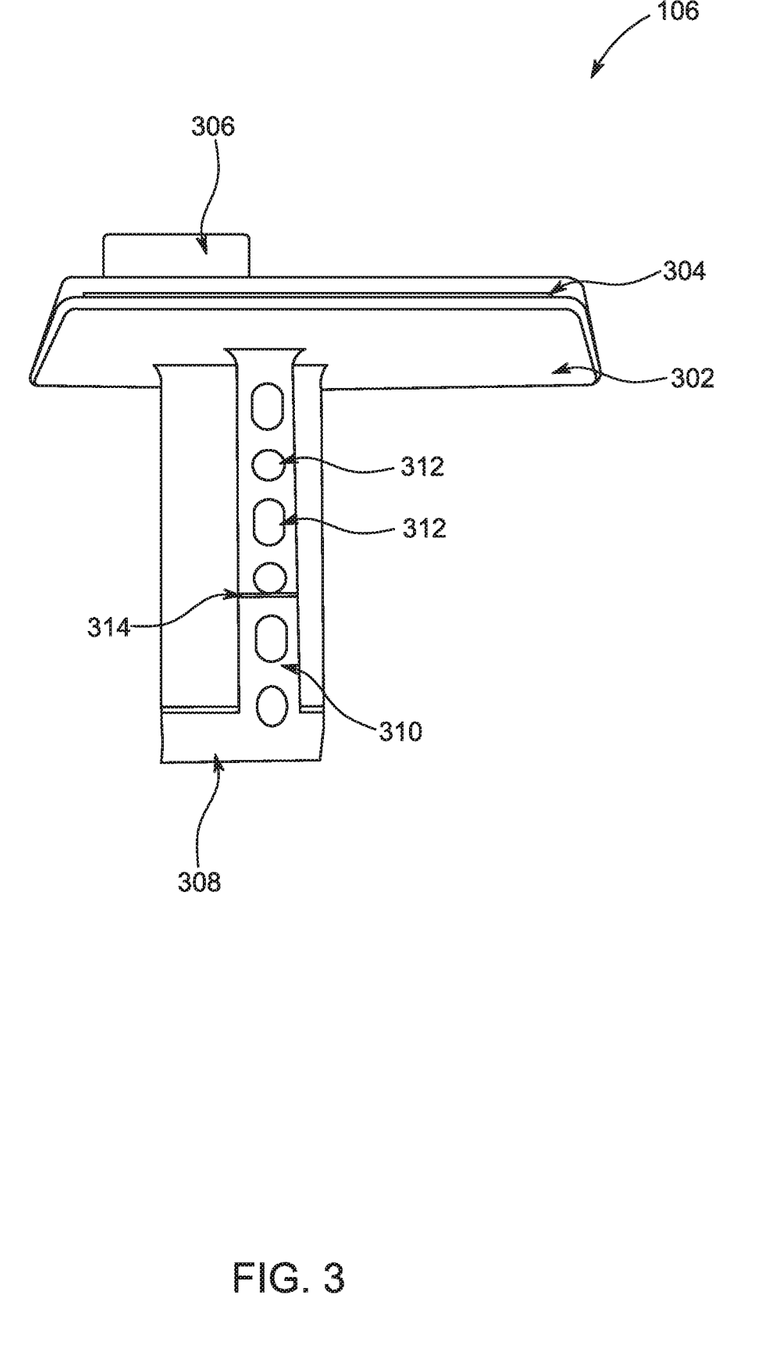
FIG. 3 is a diagram showing an exemplary embodiment of a cutting guide element of the cutting block for total knee arthroplasty.

In another exemplary embodiment illustrated in FIG. 3, the cutting guide 106 may include a frame 302 having an opening 304 extending from the anterior face to the posterior face to guide a saw blade to cut the femur. A slide 308 may extend from a frame 302 and may be translatably engaged in the space defined by a groove 404 and flanges 406,407 of the body 104. The slide 308 may include an extension 310 having a number of openings 312 and a point of reference 314. For example, the slide 308 may have a single opening in some embodiments or multiple openings 312 which may be utilized if additional stability is desired or required. The cutting guide may further include a connector 306 that may extend from the support frame 302 and may removably connect the feeler gauge 108 to the cutting guide 106 by a mechanism such as a spring-loaded ball locking system or any desired mechanism, as may be understood by a person having ordinary skill in the art. It may also be appreciated that the angle of the anterior cut of this guide may match the definitive cut needed for the implant. For example, the anterior cut of cutting guide 106 can be utilized to provide the precise cut needed for the implant without further tooling or evaluation, and eliminating potential errors or unnecessary or undesired cuts.

Figure 4:
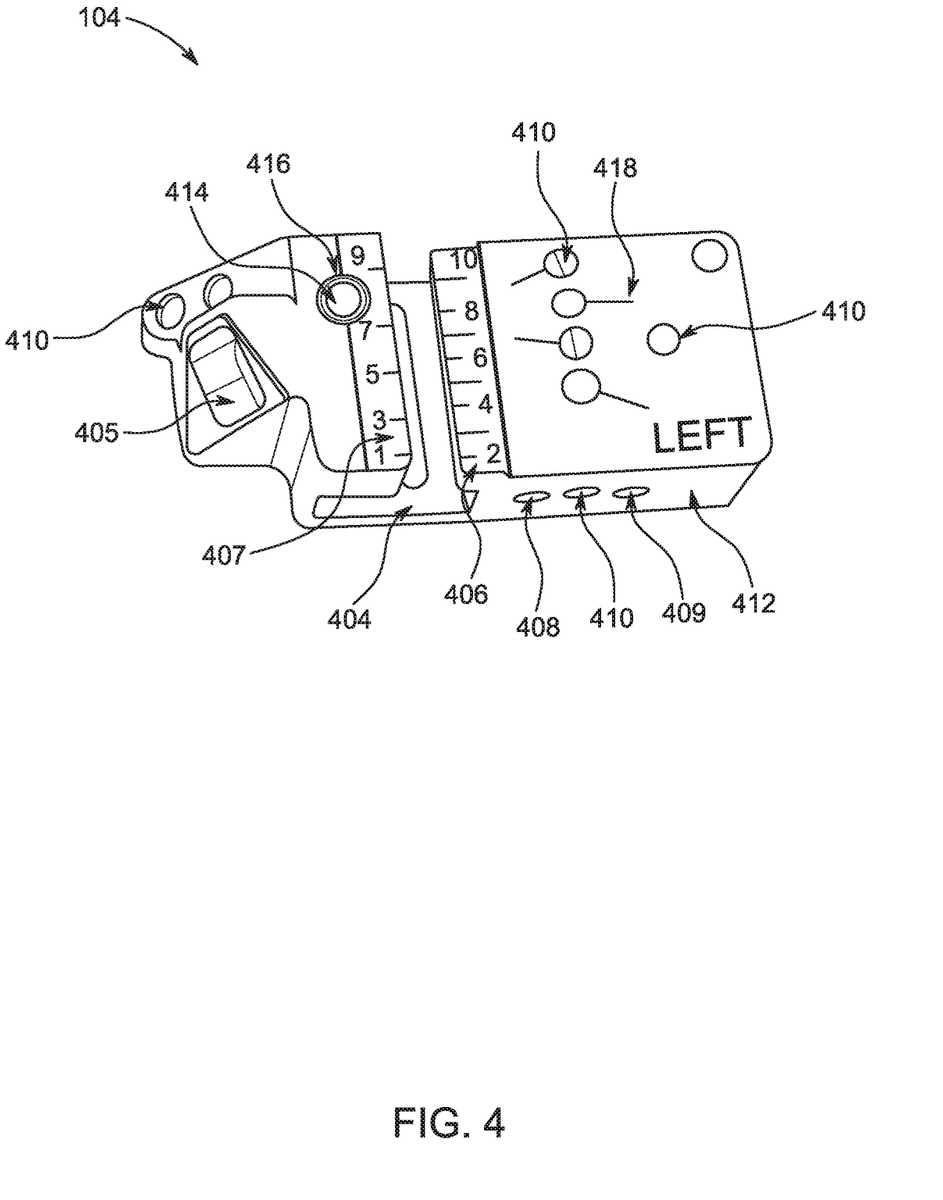
FIG. 4 is a diagram showing an exemplary embodiment of a body element of the cutting block for total knee arthroplasty.
Figure 7:
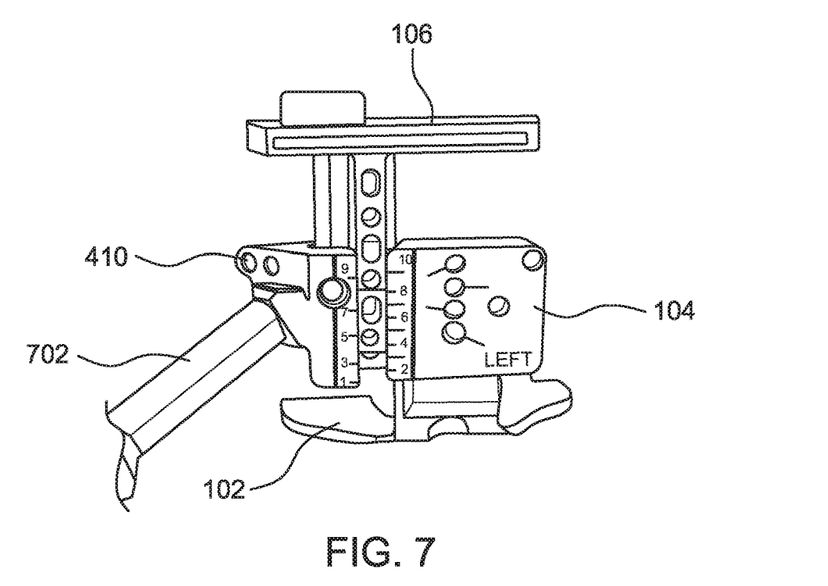
FIG. 7 is a diagram showing an exemplary embodiment of a cutting block for total knee arthroplasty with a quick connect piece inserted.

In an exemplary embodiment illustrated in FIG. 4, the body 104 may include a flat surface 412 that may have at least one opening 410 receiving any desired locking screws or bolts and a number of openings 408, 409 that may receive pegs 205, 206. It may further be appreciated that at least one opening 410 may allow for the insertion or receipt of pegs 205, 206 in such a fashion that they would not interfere with any cutting or desired motion of a saw blade. Additionally, at least one opening 410 may be accompanies by guide line 418. Guide line 418 may provide an orientation or direction for the insertion of pegs 205, 206. Additionally, after insertion, pegs 205, 206 may not be clearly visible outside of body 104; therefore guide lines 418 can provide a viewer or user with a clear indication of the orientation and direction of inserted pegs 205, 206. The body 104 may have a groove 404 with flanges 406, 407. The space defined by the groove 404 and the flanges 406,407 may receive the slide 308 extending from the frame 302 of the cutting guide 106. Flanges 406 and 407 may have graduations that may be aligned with the number of point of reference 314 that may be marked on the cutting guide 106. The graduations may be calibrated for the different available sizes and styles of implants, as may be understood by a person of ordinary skill in the art. A locking screw 414 in receiver 416 may be threadably engaged in a threaded opening of the body 104. When the user tightens the locking screw 414, the locking screw may bear against the slide 308 of the cutting guide 106 and may lock the cutting guide 106 against the body 104, as may be understood by a person of ordinary skill in the art. Additionally, socket 405 may be provided on a front portion of body 104. Socket 405 may be such that it can receive an item or apparatus, such as a connector, rod or arm, may be inserted there through. This is further shown in exemplary FIG. 7 and item 702. Further, it may be appreciated that given the orientation of socket 405, a connector, arm or rod may be inserted therein while still allowing a drill or pin driver to have unrestricted or otherwise desired access to holes 410 proximate socket 405.

Figure 5A:
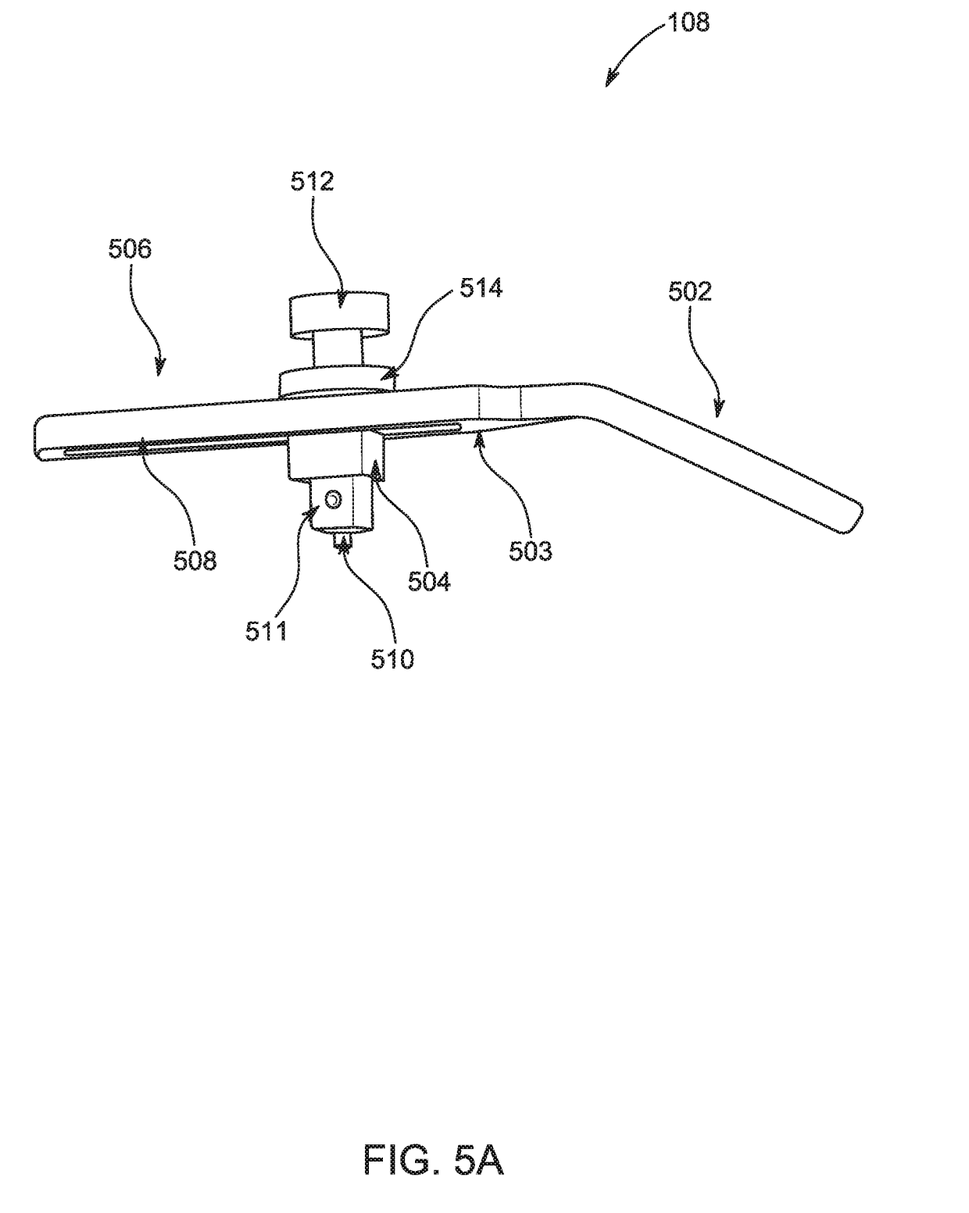
FIG. 5A is a diagram showing an exemplary embodiment of a feeler gauge element of the cutting block for total knee arthroplasty.

In an exemplary embodiment illustrated in FIG. 5A, the feeler gauge 108 may include a support block 504 that may receive a pointer arm 503. The pointer arm 503 may include a pointer 502 that may contact patient bone tissue during referencing. A longitudinal slot 508 in pointer arm 503 may allow bolt 512 to pass there through and may form a connection with the support block 504. The pointer arm 503 may receive a washer 514 having an opening there through. The element 514 may provide a bearing member for interfacing between the bolt 512 and the pointer arm 503. The bolt 512 may be a spring loaded, depressible element which can operationally control a locking or seating mechanism, such as spring loaded ball 511. For example, when bolt 512 is depressed, ball 511 may be retracted inside the body of connector 510. This can further allow connector to be fitted and securely coupled into a receiving portion of connector 306. This arrangement can further allow pointer arm 503 to maintain a free range of motion. A connector 510 may extend from the support block 504 and may removably connect the feeler gauge 108 to the cutting guide 106 by the spring-loaded ball 511, or any other coupling or locking system or mechanism, as desired. It may be further appreciated that an angle matching the angle of the anterior cut relative to the distal cut for the implant may be incorporated. The value of the angle may be, for example, 3 degrees. It may be further appreciated that the value of the angle may be anywhere from zero degrees to seven degrees or more.

Figure 5B:
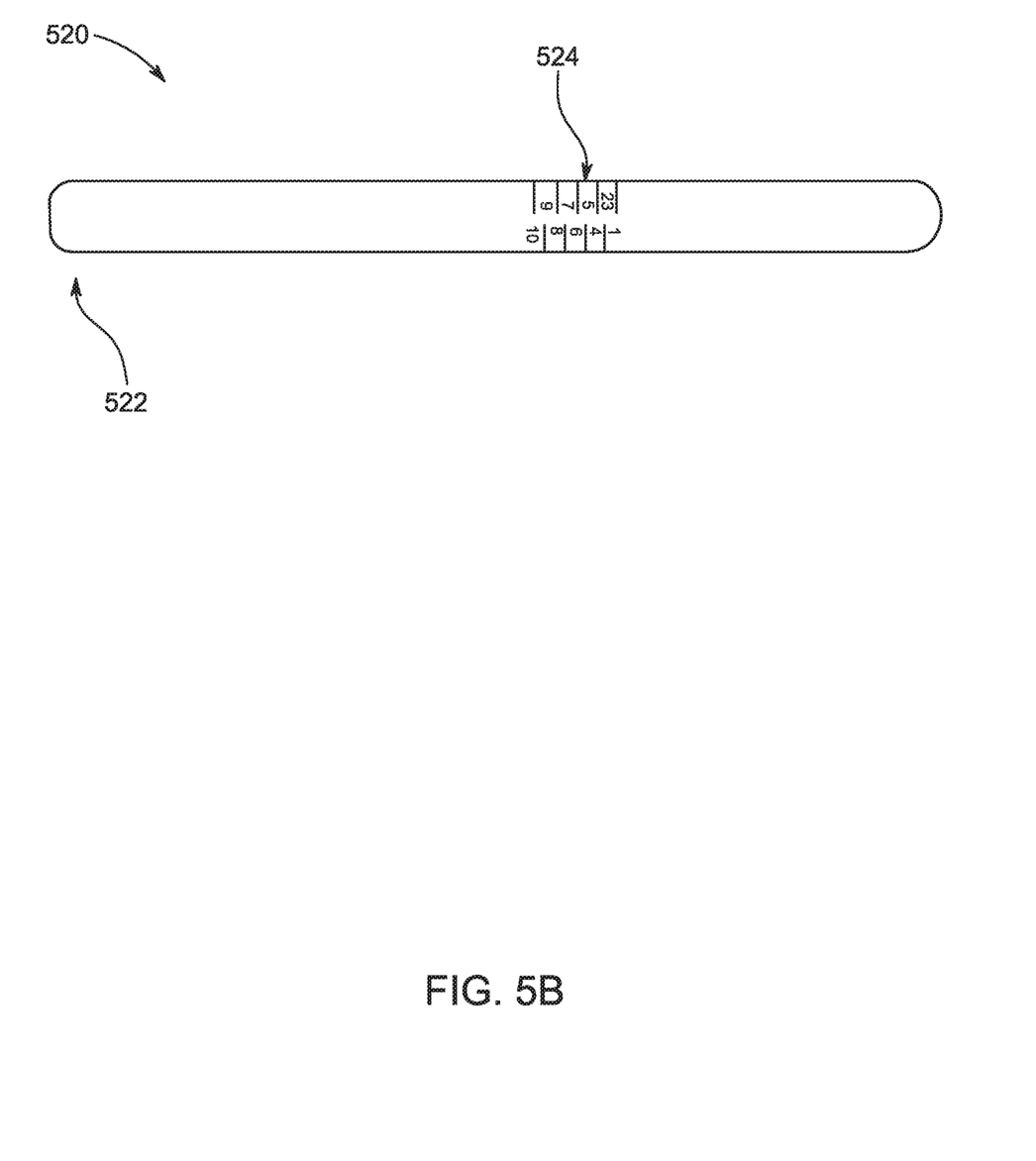
FIG. 5B is a diagram showing an exemplary embodiment of a ruler element of the cutting block for total knee arthroplasty.

In an exemplary embodiment illustrated in FIG. 5B a ruler 520, which may be formed of a metal or other material, as desired, may be utilized with other exemplary embodiments as described herein. The metal ruler 520 may have an essentially elongated shape with a first end 522 and a second end 524 that may bear markings or graduations. The metal ruler 520 may be marked according to the size and position of the implants and may have a thickness allowing it to fit through the saw guide. The anterior femur may be cut sequentially until the ruler 520 measurement is the same as where the point of reference 314 lines up with the calibration 406 and 407. It may be appreciated that the ruler 520 may be chosen and calibrated for the style of implant selected. Bone may be removed anteriorly until the anterior-posterior (AP) dimensions as read on the measuring and cutting block 100 matches the proximal/distal depth of the anterior cut. For example, in operation, bone may be removed systematically and/or repeatedly until desired dimensions on the measuring and cutting block 100 match the proximal/distal depth of the anterior cut. This provides the advantageous result of allowing a user to remove precise amounts of bone incrementally until a desired depth is achieved. For example, locking screw 414 may be tightened so that feeler gauge 108, inserted through body 104, can act as a positioning guide and, also, provide an approximately 1 mm range of motion for a saw blade. After an initial cut, locking screw 414 may be loosened and tightened to adjust the position of body 104 and incremental cuts can be made to ensure proper sizing and fitment of an implant with a femur of a patient.

In another exemplary embodiment, a chamfer block system may be a variation of a traditional block. The size and shape of the chamfer block may be designed to match the implant and the underside of the block may be smooth in preference to having fixed pins. Further, a shim may be added to the chamfer block for proper placement.

It may also be appreciated that screw fixation of the chamfer block may be superior to the standard pin fixation, particularly in soft bone. Further, the size and shape of the cutting block may be designed to match the size and shape of the corresponding implant. The matching shape of the block to the implant may facilitate medial and lateral positioning of the block that may be particularly important for knee designs with pegs.

In another exemplary embodiment, the measuring and cutting block 100 may be combined with patient specific instruments so as to maximize the benefits of each and decrease the costs of the cutting block 100. In one such embodiment, the measuring and cutting block 100 may be used after the distal cut may be made with patient specific instruments. The measuring and cutting block 100 may be customized, as patient specific technology may be used to select or create custom feet to better match the patient's rotation. Thus, the rotation may be set by either a custom foot piece with the proper rotation built in, or by selecting from a series of pre-made feet with different available rotations (for example, every half-degree), as may be understood by a person having ordinary skill in the art.

The system may be further modified to accommodate any desired implant including, but not limited to, JURNEY, LEGION, or the ACL/PCL sparing designs by simply varying the calibration on the metal ruler 520 and flanges 406, 407, as may be understood by a person having ordinary skill in the art.

In a further exemplary embodiment, a chamfer block may be included in the system. The chamfer block may have openings for any desired types of fasteners, such as screws, that may be used with implants having pegs in each femoral condyle, as may be understood by a person of ordinary skill in the art. Screws may be utilized to drill holes for the pegs. Systems without pegs on the implant may still use screws. Screws may be an alternative to pins for the fixation of the block. The pins may be about 1 mm in diameter and smooth and the screw may be 6.5 mm surgical screws. It may be appreciated that any desired type and size of screws and pins may be utilized, as may be understood by a person of ordinary skill in the art. Additionally, it may be understood that 6.5 mm surgical screws can provide an improved, more stable fixation than commonly utilized 1 mm pins.

Figure 6:
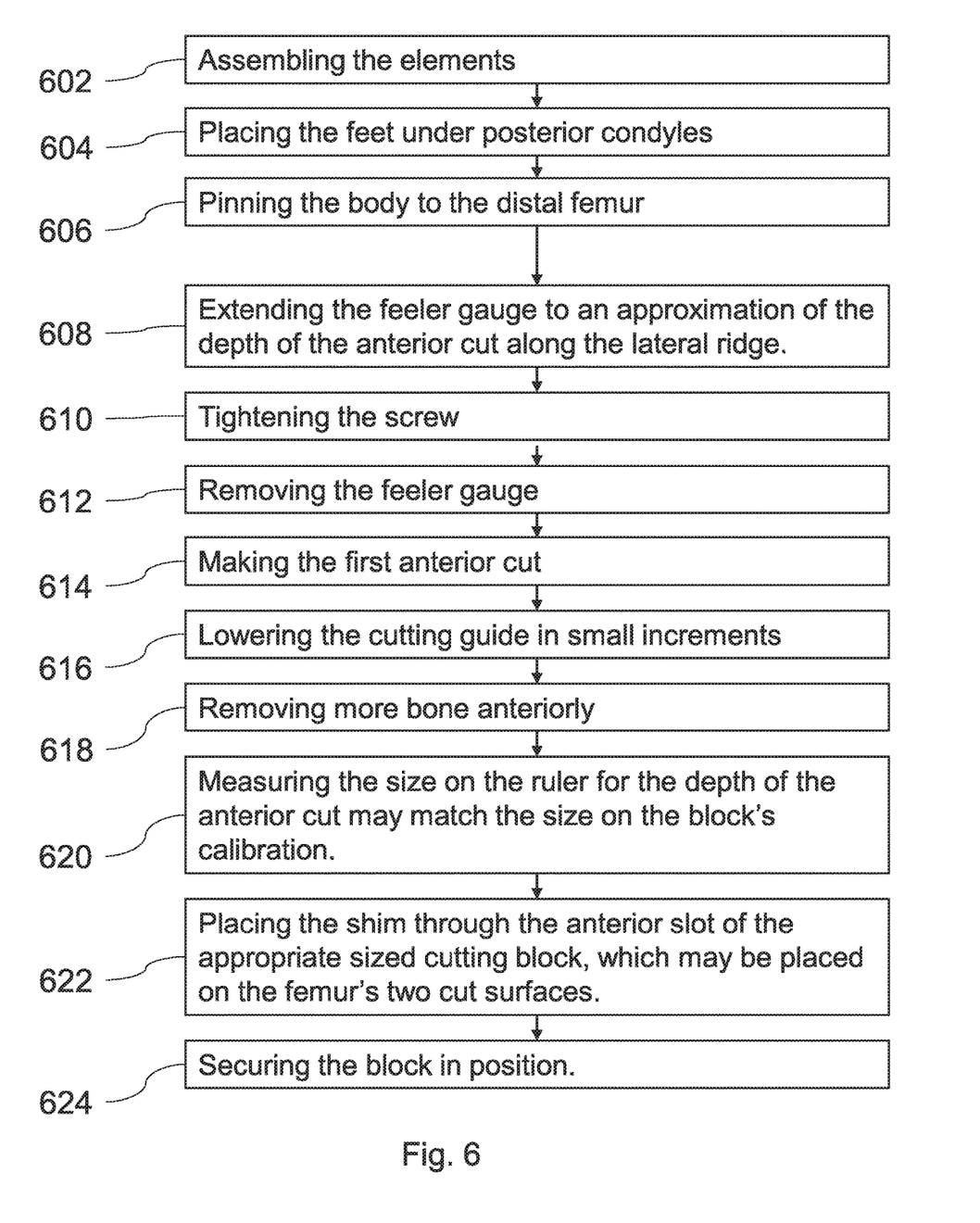
FIG. 6 is a diagram showing an exemplary embodiment of a method of total knee arthroplasty.

According to another exemplary embodiment, a method of total knee arthroplasty may be provided. It may be appreciated that the steps described herein may be carried out using the various components shown and described in the various embodiments. The method of total knee arthroplasty may include the steps of assembling the elements 602 before placing the feet under posterior condyles 604 and pinning the main block to the distal femur 606. The feeler gauge may be extended to an approximation of the depth of the anterior cut along the lateral ridge 608 before tightening the screw 610. Once the screws are secure, the feeler gauge may be removed 612. A safety may be built into the feeler gauge and may be about 1 mm or any desired height, as may be appreciated by a person having ordinary skill in the art. The next step may then include making the first anterior cut 614 and lowering the cutting guide in small increments 616 to remove more bone anteriorly 618. The removal of small increments may prevent notching of the anterior femur and bone may be removed anteriorly until the AP dimension as read on the measuring and cutting block 100 matches the proximal/distal depth of the anterior cut. This procedure allows for the proper AP positioning of the implant. It may be appreciated that this shaving process may eliminate the possibility that the saw blade may catch under more proximal femoral bone and notch, as may be understood by a person of ordinary skill in the art.

Further steps included in the method of total knee arthroplasty may be measuring the size on the ruler 520 for the depth of the anterior cut matches the size on the block's calibration 620. It may be appreciated that a ruler 520 calibrated for the style of implant may be selected and the anterior cut may be optimized by measuring depth of the anterior cut after one or a few cuts, as desired. In the next step, the shim may be placed through the anterior slot of the appropriate sized cutting block, which may be placed on the femur's two cut surfaces 622. It may be appreciated by a person having ordinary skill in the art that the removal of small increments may prevent notching of the anterior femur. Once the position is set, the block may be pinned in position. It may be appreciated that the size and shape of the block medial to lateral may match the size and shape of the implant, the user may accurately appraise if the size of implant that matches the AP dimension of the femur may also match the ML dimension. If it is too wide, the user may downsize without fear of notching, the anterior cut may be already optimal, as may be understood by a person of ordinary skill in the art.

In another exemplary embodiment, the cutting block and method for total knee arthroplasty described herein may have some additional benefits to the company as well as to the patient and surgeon. The described cutting block and method for total knee arthroplasty may be simpler in design and manufacturing than other distal femoral cutting systems.

The foregoing description and accompanying figures illustrate the principles, preferred embodiments, and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A cutting block for cutting a femur during knee arthroplasty surgery, the cutting block comprising:
    a cutting guide having one slot for guiding a saw blade to cut the femur, the cutting guide having an anterior face and a posterior face, the cutting guide comprising a single femoral cut slot extending continuously on a flat surface from the anterior face to the posterior face to guide the saw blade to cut the femur and further comprising a slide extending from a frame of the cutting guide;
    a body having a groove with flanges, wherein a space defined by the groove with flanges receives the slide extending from the frame of the cutting guide, a face of the body creates a substantially flat surface surrounding the groove with flanges, and further having a locking screw, threadably engaged in a threaded opening of the body, that is configured to bear against the cutting guide and lock the cutting guide against the body, and the threaded opening sits flush with the body;
    a feeler gauge including at least one of a support block and a pointer arm, wherein the pointer arm includes a pointer configured to make contact with patient bone, the feeler gauge further rotatable to engage the femur medially and laterally; and
    a foot including a pair of spaced apart projections configured to engage posterior condyles of the femur, wherein the cutting block further comprises a calibrated ruler disposed on the cutting block, a height of the cutting guide is adjustably configured to receive the calibrated ruler so as to measure proximal to distal depth of the anterior cut, wherein the height of the cutting guide adjusts to match a depth of a femoral cut.

2. The cutting block of claim 1, wherein the slide extending from the frame is translatably engaged in the space defined by the groove with flanges.

3. The cutting block of claim 1, wherein the slide includes an extension having at least one opening and at least one point of reference.

4. The cutting block of claim 1, wherein the frame of the cutting guide includes a connector configured to connect the feeler gauge to the cutting guide removably.

5. The cutting block of claim 4, wherein the connector includes a locking mechanism comprising a spring-loaded ball.

6. The cutting block of claim 1, wherein the body includes at least one of a flat surface that has at least one opening receiving at least one of a locking screw, bolt, and peg.

7. The cutting block of claim 1, wherein the flanges have graduations configured to align with at least one point of reference marked on the cutting guide.

8. The cutting block of claim 7, wherein the graduations are calibrated for different available sizes of implants.

9. The cutting block of claim 1, wherein a longitudinal slot in the pointer arm allows a bolt to pass therethrough and forms a connection with the support block.

10. The cutting block of claim 1, wherein the pointer arm receives a washer having, an opening therethrough and providing a bearing member for interfacing between a bolt and the pointer arm, wherein the bolt is threadably engaged in a threaded opening of the support block, and wherein the washer is configured to bear against the pointer arm and to lock the pointer arm against the support block when tightened.

11. The cutting block of claim 1, wherein a connector extends from the support block and removably connects the feeler gauge to the cutting guide.

12. The cutting block of claim 11, wherein the connector includes a spring-loaded ball locking mechanism.

13. The cutting block of claim 1, wherein the foot includes a space between the projections.

14. The cutting block of claim 1, wherein a pair of spaced apart pegs on the foot fits corresponding openings in the body.

15. The cutting block of claim 1, wherein a base member extends between projections configured to engage posterior condyles of the femur and pegs, wherein the base member provides a flat surface registering snugly against the body.

16. The cutting block of claim 15, wherein the base member includes a threaded opening there through configured to receive a screw locking the foot against the body, and the foot is curved to fit substantially flush against a tibial surface.

17. A system for performing a knee arthroplasty surgery on a knee portion of a leg of a patient through an incision, comprising:
    a cutting block, comprising:
        a cutting guide, comprising:
            at least one slot for guiding a saw bade to cut the femur,
            an anterior face and a posterior face,
            a femoral cut slot extending from the anterior face to the posterior face to guide a saw blade to cut the femur, and
            a slide extending from a frame of the cutting guide so that the anterior femur can be cut in small increments;
        a body, comprising:
            a groove with flanges, wherein a space defined by the groove with flanges receives the slide extending from the frame of the cutting guide, wherein a main body is pinned to the distal femur,
            a locking screw, which is threadably engaged in a threaded opening of the body, wherein the locking screw bears against the cutting guide and locks the cutting guide against the body;
        a feeler gauge including at least one of a support block and a pointer arm, wherein the pointer arm includes a pointer configured to make contact with patient bone tissue and is extended to an approximation of the depth of the anterior cut along the lateral ridge, locked into place, and then removed prior to the first anterior cut, and
        a foot including a pair of spaced apart projections configured to engage the posterior condyles of the patient's femur, wherein the cutting block further comprises a calibrated ruler disposed on the cutting block, a height of the cutting guide is adjustably configured to receive the calibrated ruler so as to measure proximal to distal depth of the anterior cut, wherein the height of the cutting guide adjusts to match a depth of a femoral cut, and the cutting block is configured to match the position of the anterior to posterior cut with the depth of the distal to proximal cut.

* * * * *